United States Patent [19]

Outtrup et al.

[11] Patent Number: 4,970,158

[45] Date of Patent: Nov. 13, 1990

[54] BETA AMYLASE ENZYME PRODUCT, PREPARATION AND USE THEREOF

[75] Inventors: Helle Outtrup, Ballerup; Barrie E. Norman, Farum, both of Denmark

[73] Assignee: Novo Industri A/S, Bagsvaerd, Denmark

[21] Appl. No.: 15,239

[22] Filed: Feb. 17, 1987

[30] Foreign Application Priority Data

Feb. 19, 1986 [DK] Denmark ............................. 0770/86

[51] Int. Cl.[5] .......................... C12N 9/26; C12N 1/20
[52] U.S. Cl. ................................. 435/201; 435/252.5; 435/95; 435/832
[58] Field of Search ................ 435/201, 95, 253, 832, 435/252.5

[56] References Cited

U.S. PATENT DOCUMENTS

| 3,868,464 | 2/1975 | Kozze et al. | 426/48 |
| 4,560,651 | 12/1985 | Nielsen et al. | 435/95 |
| 4,604,355 | 8/1986 | Outtrup | 435/95 |
| 4,647,538 | 3/1987 | Zeikus et al. | 435/201 |

Primary Examiner—Elizabeth C. Weimar
Assistant Examiner—Charles L. Patterson
Attorney, Agent, or Firm—Morris Fidelman; Franklin D. Wolffe

[57] ABSTRACT

A novel beta amylase enzyme product with improved thermostability and acid-stability is provided. The novel enzyme can be produced by cultivating a newly discovered microorganism Bacillus sp. (21–51) belonging to the *Bacillus acidopullulyticus* complex and may be used alone or in combination with a variety of conventional debanching enzymes in the production of high maltose syrups.

6 Claims, 2 Drawing Sheets

BETA AMYLASE ENZYME PRODUCT, PREPARATION AND USE THEREOF

This invention relates to a novel β-amylase enzyme product, a process for its preparation, compositions containing said β-amylase in combination with other enzymes, and the use of the β-amylase or such compositions in the production of high maltose syrups.

BACKGROUND OF THE INVENTION

β-amylase is the name traditionally given to exacting maltogenic amylases which catalyze the hydrolysis of 1,4-α-glucosidic linkages in amylose, amylopectin and related glucose polymers Maltose units are successively removed from the non-reducing chain ends in a stepwise manner until the molecule is degraded or, in the case of amylopectin, until a branch point is approached. The maltose released has the β anomeric configuration hence the name β-amylase.

The β-form of maltose will in aqueous solutions, isomerize spontaneously to a mixture of the α- and β-forms. Prolonged reaction of β-amylase on amylopectin or partially degraded amylopectin, results in the formation of β-limit dextrin i.e. material which is not susceptible to further hydrolysis by β-amylase.

β-amylases may be used to produce maltose containing syrups of use in the confectionary, baking, and brewing industries.

In the production of high maltose syrups β-amylases are conventionally used in combination with debranching enzymes in order to increase the maltose content in the product by hydrolyzing the 1,6-α-glucosidic bonds in the β-limit dextrins.

β-amylases have been isolated from various plants and microorganisms (W. M. Fogarty and C. T. Kelly, Progress in Industrial Microbiology, vol. 15, p. 112–115, 1979). These β-amylases are characterized by having optimum temperatures in the range from 40° C. to 65° C. and optimum pH in the range from 4.5 to 7.

Debranching enzymes exhibit for the most a pH optimum in the range from 3.5 to 6 and are thus more active in an acid solution. In the use of β-amylases and debranching enzymes in combination the pH chosen is usually a compromise between the pH optimum of each of the chosen enzymes or the enzymes are used in succession.

In a process for the production of maltose wherein starch in an aqueous solution is hydrolyzed by a β-amylase it is also an advantage to use temperatures at or above 60° C. in order to inhibit retrogradation and to avoid microbial infections.

The vegetal β-amylases further have the disadvantage that their production require large amounts of raw material and a large energy consumption for the extraction and processing, whereas microbial β-amylases can be produced on a large scale at relatively low costs.

One maltogenic amylase has been disclosed in U.S. patent application Ser. No. 591,460, filed on Mar. 3, 1984, now U.S. Pat. No. 4,604,355, which amylase is sufficiently thermostable to be used at temperatures in the range from 60° C. to 65° C. However, this enzyme has its pH optimum at pH 4.5 to 5.5. Also, the enzyme according to said U.S. patent application hydrolyzes maltotriose, which results in the production of glucose.

In high maltose syrups the presence of glucose should be avoided, and the use of said maltogenic amylase consequently requires subsequent removal of the glucose produced to a satisfactory level.

Therefore, there still exists a need for an effective microbial β-amylase preparation which is sufficiently thermostable to be employed at 60°–70° C. for extended periods of time to allow hydrolysis of the starch in an economical way, is sufficiently stable at pH values below 5 to allow for simultaneous hydrolyzation of starch by the β-amylase and a debranching enzyme under optimal conditions, and which in the production of high maltose syrups does not produce excessive amounts of glucose, which in some cases subsequently must be separated from the syrup.

It is an object of the present invention to furnish a novel microbial β-amylase which has a high temperature stability, a pH optimum at pH values below 5 and which produce minimal amounts of glucose.

The present invention is based upon the discovery that a novel microbial extracellular β-amylase (21-51 β-amylase) having such properties is produced from a newly isolated Bacillus strain NCIB 11608.

For better understanding of the invention herein and the description which follows, attention is directed to the attached drawing wherein:

FIG. 1 is a plot of relative activity of the maltogenic enzyme against temperature; and FIG. 2 is a plot of relative activity against pH.

SUMMARY OF THE INVENTION

According to its first aspect, the present invention provides a β-amylase enzyme product which comprises a novel thermostable β-amylase having the following characteristics:

(a) it is obtainable by cultivation in a suitable nutrient medium of a Bacillus strain with the deposit number NCIB 11608.

(b) it exhibits the enzyme chemical properties of the β-amylase derived from the Bacillus strain NCIB 11608, (c) its activity optimum measured at 30 min reaction time in acetate buffer (0.1M) at pH 4.5 is about 70° C., (d) its pH optimum is at 30 min reaction time in the range of 4–5 as determined in a McIlvaine buffer at about 60° C.

According to its second aspect, the present invention provides a process for the preparation of the above thermostable β-amylase enzyme product which process comprises the cultivation of the above mentioned Bacillus, strain NCIB 11608 or variants or mutants thereof productive of this enzyme in a suitable nutrient medium containing carbon and nitrogen sources and inorganic salts, optionally followed by recovery of the β-amylase enzyme product According to a further aspect the present invention provides a process for the production of high purity maltose syrups wherein starch is treated with the novel β-amylase enzyme product in an aqueous medium.

Tests have shown that the novel β-amylase enzyme product is suitable for the production of maltose and high maltose syrups. Such products are of considerable interest for the production of certain confectioneries because of the low hygroscoposity, low viscosity, good heat stability and mild, not too sweet taste of maltose.

The industrial process of producing maltose syrups comprises liquefying starch, then saccharification with a maltose producing enzyme, and optionally with an enzyme cleaving the 1,6-branching points in amylopectin, for instance pullulanase or isoamylase.

In a still further aspect the present invention provides an active enzymatic composition comprising the novel β-amylase product in combination with at least one debranching enzyme.

According to another aspect the present invention provides a process for the production of high purity maltose syrups, wherein starch is treated with the novel active enzymatic composition of the invention.

By using the novel enzymatic composition it is possible to conduct the above mentioned saccharification of the starch under optimal pH conditions, whereby the yield of maltose is increased and the amount of added enzyme may be reduced.

21-51 β-amylase hydrolyzes amylopectin, glycogen, and amylose, releasing only β-maltose.

From branched polysaccharides, such as amylopectin and partially hydrolyzed amylopectin 21-51 β-amylase forms β-limit dextrins, which can be hydrolyzed by glucoamylase, isoamylase, pullulanase, or the like.

21-51 maltogenic amylase differs from other Bacillus β-amylases in the following respects:
1. It is stable in buffer at 70° C.,
2. It is stable in a pH range from 4.0 to 5.0, which means that it can be used in combination with debranching enzymes such as isoamylase and pullulanase.
3. glucose is only produced in minimal amounts.

DETAILED DESCRIPTION OF THE INVENTION

Figure 1:
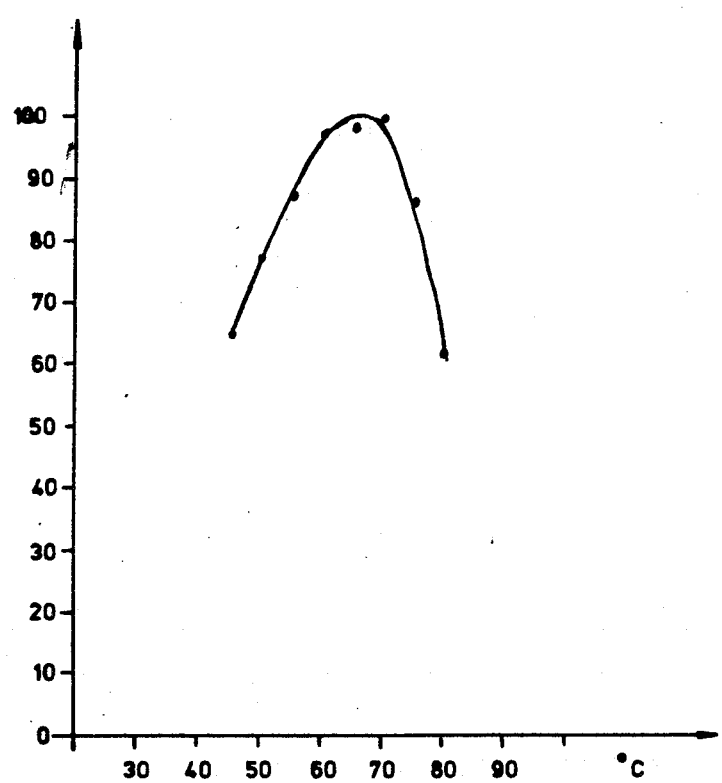

The microorganism capable of producing the β-amylase according to the present invention was selected by means of its ability to grow on an agar substrate prepared as follows:

Tryptone (10 g), amylopectin (CPC snowflake 10 g), Bacto agar (40 g), and deionized water (1000 ml) are mixed aseptically at 55° C. with an equivalent amount of a salt solution of the following composition:

| | |
|---|---|
| $(NH_4)_2SO_4$ | 0.04% by weight |
| $MgSO_4, 7H_2O$ | 0.1% by weight |
| $CaCl_2$ | 0.05% by weight |
| $KH_2PO_4$ | 0.6% by weight | the pH of the salt solution being adjusted to 3.0 with 10N sulphuric acid.

The isolated microorganism was deposited with the National Collection of Industrial Bacteria (NCIB), Torry Research Station, Aberdeen, Scotland, on Mar. 15, 1983 and accorded the reference number NCIB 11608 NCIB, being an international depository authorized under the Budapest Treaty of 1977, affords permanence of the deposit and accessability thereto to the public in accordance with rules 9 and 11, respectively, of said treaty.

TAXONOMY

Morphology

Rod-shaped bacteria having a diameter of 0.6 to 0.8 μm.

The spores are oval to cylindrical in form, placed centrally to subterminally and do not cause swelling of the sporgania.

Biochemical Reactions

| Biochemical Reactions | |
|---|---|
| Gram colour: | Positive, |
| Anaerobic growth: | Negative, |
| Catalase: | Positive, |
| VP reaction: | Negative, |
| Nitrate reduction: | Positive, |
| Lecithinase: | Negative, |
| Growth in 3.5% NaCl: | Negative, |
| Hydrolysis of: | |
| starch: | Positive, |
| Casein: | Weakly positive, |
| Acid production from: | |
| Glucose: | Positive, |
| Arabinose: | Negative, |
| Xylose: | Negative, |
| Mannitol: | Positive, |
| Utilization of: | |
| Citrate: | Negative, |
| Propionate: | Negative, and |
| Growth at 50° C.: | Negative. |

The Bacillus NCIB 11608 do not grow on conventionally used media with a pH above 6. The optimal conditions of growth for this bacterium are pH 4.8 to 5.8 and a temperature of 30° to 37° C.

The maximal temperature for growth of the bacterium is 45° C.

In the above tests a standard medium containing equal amounts of 1% tryptone and BA-1 salts was used.
BA-1 salts comprise.
$(NH_4)_2SO_4$ 0.04%
$MgSO_4.7\ H_2O$ 0.1%
$CaCl_2.2\ H_2O$ 0.05%
$KH_2PO_4$ 0.6% pH is adjusted to 3.0 with 10N $H_2SO_4$ prior to autoclaving.

pH in the ready-mixed tryptone basis medium is 4.8 to 5.2.

All the above biochemical reactions and growth tests were performed on this substrate with or without addition of 1% yeast extract.

The standard growth medium for the proliferation of NCIB 11608 contains 0.5% amylopectin and no yeast extract. Vegetative cells of NCIB 11608 do often contain bubbles which in a phase contrast microscope appear as refractive spheres, and which are not coloured when the cells are lightly stained by safranin or methylene blue.

The morphological and biochemical properties are very much like those that characterize *Bacillus megaterium*, but the properties of the beta amylase are very far from those that till now have been described for *Bacillus megaterium* beta amylase The microorganism is believed to belong to the *Bacillus acidopullulyticus* complex described in U.S. Pat. No. 4,560,651.

Determination of Enzyme Activity

One β-amylase unit (βU) is defined as the amount of enzyme which under standard conditions (temperature 60° C., pH 4.5, and reaction time 30 minutes) produces reducing sugar corresponding to 1 μmol maltose per minute 0.5 ml 2% starch in 0.1M acetate buffer is incubated with 100 μl of the enzyme dissolved in deionized water containing 0.5-2 βU per ml. The reaction is stopped after 30 minutes by addition of 0.3 ml 0.5N NaOH, and the mixture diluted in a ratio of 1:10 with deionized water.

The content of reducing sugar is then determined by means of the Somogyi method (Somogyi: J. Biol. Chem., 153, p. 375–80 (1944)).

ENZYME PREPARATION

A Bacillus strain capable of producing the β-amylase of the present invention is usually propagated on a solid substrate prior to its cultivation under aerobic conditions in a suitable fermentation medium. Both media contain assimilable sources of carbon and nitrogen besides inorganic salts optionally together with growth promoting nutrients, such as yeast extract The fermentation is typically conducted at 30°–37° C. and at a pH of 5–6 and preferably kept approximately constant by automatic means. The enzyme is excreted into the medium.

The ensuing fermentation broth may be freed of bacterial cells and debris therefrom together with other solids, for example by filtration. The supernatant containing the enzyme may be further clarified, for example by filtration or centrifugation, and then concentrated as required, for example by ultrafiltration or in an evaporator under reduced pressure to give a concentrate which, if desired, may be taken to dryness, for example by lyophilization or spray-drying.

Purification of Enzyme

The maltogenic amylase of the present invention can be purified from a continuous fermentation culture broth as follows:

250 liters of culture broth is filtered and the filtrate is ultrafiltered, germ filtered, and freeze-dried.

The powder is dissolved in 15 mM acetate buffer, pH 5.0 and dialysed against 15 mM acetate buffer pH 5.0 until the conductivity is about 1 mS. The dialyzate is then applied to a cation exchanger CM-sepharose Cl-6B which has been equilibrated with the same buffer. The amylase passes through the column whereas 60% of the remaining proteins is withheld by the ion-exchanger.

The pH of the effluent from this column is adjusted to 4.0 with acetic acid and the eluate is subsequently applied to a CM-sepharose Cl-6B column equilibrated with 15 mM acetate buffer pH 4.0. Under these circumstances the amylase is adsorbed by the ion-exchanger. The enzyme is then eluated with acetate buffer of pH 4.0 with increasing ionic strength. The enzyme activity in the eluate follows the protein content in a symmetrical peak.

Enzyme Chemical Properties

The dependence of the activity of the β-amylase of this invention on pH and temperature was determined by the method described above using a reaction mixture in which pH and temperature were adjusted to predetermined values.

Reference is again made to the attached drawings in which

Figure 2:
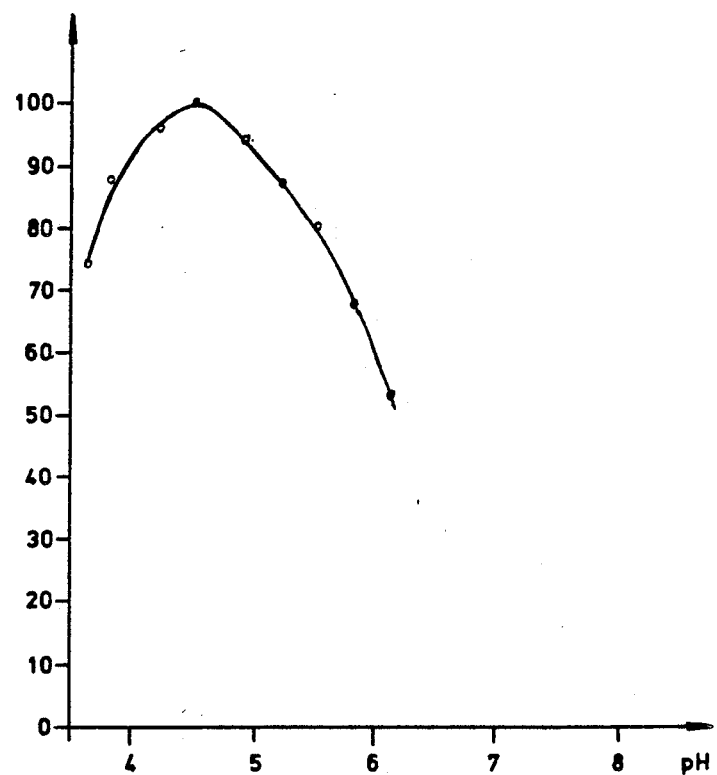

FIG. 1 graphically illustrates the relative activity plotted against temperature (substrate 2% soluble starch, pH 4.5 (0.1M acetate), 30 minutes reaction time), and FIG. 2 graphically illustrates the relative activity plotted against pH (temp. 60° C., substrate 2% soluble starch, 30 minutes reaction time, McIlvaine buffer).

It appears from the drawings that 21-51 β-amylase has an activity optimum at pH 4.5 of about 70° C. and that its pH optimum is in the range of 4.0–5.0. More than 60% of the maximum activity is still found at 80° C.

EXAMPLE 1

Preparation of β-amylase from Bacillus sp. 21–51, deposit number NCIB 11608

Inoculum

The 21-51 culture was grown at 37° C. for 2 days on the following agar:

| | |
|---|---|
| Tryptone | 10 g |
| Amylopectin (CPC snowflake) | 10 g |
| Bacto agar | 40 g |
| Deionized water | 1000 ml | mixed with an equivalent amount of a salt solution of the following composition:

| | |
|---|---|
| $(NH_4)_2SO_4$ | 0.04% by weight |
| $MgSO_4, 7H_2O$ | 0.1% by weight |
| $CaCl_2$ | 0.05% by weight |
| $KH_2PO_4$ | 0.6% by weight | the pH of the salt solution being adjusted to 3.0 with 10N $H_2SO_4$.

Continuous Fermentation

Continuous fermentation was carried out with a substrate having the following composition:

| | |
|---|---|
| Difco Yeast Extract 0.2% | 0.2% |
| Corn steep liquour | 1.0% |
| $(NH_4)_2SO_4$ | 0.1% |
| $MgSO_4.7H_2O$ | 0.0375% |
| $K_2HPO_4$ | 0.0375% |
| $CaCl_2.2H_2O$ | 0.0375% |
| Bacto Tryptone | 0.4% |
| Pullulan | 0.4% |
| Pluronic 60 1 | 0.08% |
| Adjusted to 100% with water, and autoclaved at 130° for 30 minutes. | |

The fermentation was carried out in a BIOFLO ® (New Brunswick, Canada) fermentor with 1 liter working volume.

The fermentation was started up with 100 ml of the above inoculum and the substrate dosage was started after 24 hours at 30° C.

The pH was adjusted to 5.5±0.2 with 3% sulphuric acid and the temperature was kept at 30° C. ±0.2.

Aerating: 0.5 liter/liter substrate/minute

Dilution rate: D=0.090 ±0.005 hr

EXAMPLE 2

Substrates for saccharificaton were prepared by redissolving a 7DE (dextrose equivalent) spray-dried maltodextrin in deionized water and making up to approximately 30% DS (dry substance). The saccharification experiments were carried out in standard 500 ml laboratory batch reactors Aliquots of the substrates were heated to 55° C. or 60° C., the pH adjusted to an initial value of 5.5, and 5 βU or 20 βU/g DS were then added. Samples were withdrawn after 4, 24, 48, 96, and 168 hours and heated in boiling water for 10 minutes to inactivate the enzyme After cooling the samples were filtered and treated with a mixedbed ion exchange resin (Bio-Rad ® AG 501×8(D)) to remove ash and soluble N before being analyzed by HPLC and gel chromatography.

The same procedure was repeated with mixtures of 5 or 20 βU/g DS of the β-amylase according to the invention and 1 pullulanase unit (PNU)/g DS pullulanase and 100 isoamylase units (IU)/g DS, respectively.

The results are shown in Table IA below.

TABLE A

Saccharification Temperature: 60° C.

| β-amylase | Pullulanase (PNU/g DS) | Reaction time (hours) | pH | % DP$_1$ | % DP$_2$ | % DP$_3$ | % DP$_{4+}$ |
|---|---|---|---|---|---|---|---|
| β-amylase 5 | 0 | 4 | 5.3 | 0.5 | 12.6 | 2.4 | 84.5 |
| | | 24 | 5.3 | 0.3 | 30.8 | 15.2 | 53.8 |
| | | 48 | 5.3 | 0.3 | 40.7 | 19.6 | 39.4 |
| | | 96 | 5.2 | 0.4 | 47.4 | 20.2 | 31.4 |
| | | 168 | 5.0 | 0.6 | 51.1 | 20.1 | 28.2 |
| 20 | 0 | 4 | 5.2 | 0.2 | 26.3 | 10.4 | 63.2 |
| | | 24 | 5.2 | 0.3 | 46.9 | 13.8 | 39.1 |
| | | 48 | 5.0 | 0.5 | 54.2 | 14.7 | 30.6 |
| | | 96 | 4.9 | 0.5 | 57.3 | 15.0 | 27.2 |
| | | 168 | 4.8 | 0.5 | 57.6 | 15.3 | 26.7 |
| 5 | 1 | 4 | 5.3 | 0.1 | 13.6 | 5.7 | 80.6 |
| | | 24 | 5.3 | 0.2 | 31.9 | 16.8 | 51.1 |
| | | 48 | 5.3 | 0.3 | 41.1 | 21.9 | 36.4 |
| | | 96 | 5.2 | 0.5 | 51.3 | 25.3 | 23.0 |
| | | 168 | 5.1 | 0.6 | 56.9 | 26.8 | 15.7 |
| 20 | 1 | 4 | 5.2 | 0.1 | 26.8 | 10.6 | 62.5 |
| | | 24 | 5.2 | 0.3 | 50.6 | 15.6 | 33.6 |
| | | 48 | 5.1 | 0.3 | 59.4 | 18.9 | 21.5 |
| | | 96 | 5.0 | 0.4 | 66.1 | 20.6 | 13.0 |
| | | 168 | 4.9 | 0.4 | 68.5 | 21.5 | 9.6 |

DP refers to the degree of polymerization, DP1 being monosaccharide(s) e.g., glucose, DP2 being disaccharides, e.g., maltose, DP3 being traisaccharides and DP4 being a saccharide oligomer with a degree of polymerization of four or more

TABLE 1B

Saccharification Temperature: 55° C.

| β-amylase | Isoamylase (IU/g DS) | Reaction time (hours) | pH | % DP$_1$ | % DP$_2$ | % DP$_3$ | % DP$_{4+}$ |
|---|---|---|---|---|---|---|---|
| β-amylase 5 | 100 | 4 | 5.2 | 0.1 | 11.4 | 5.2 | 83.3 |
| | | 24 | 5.2 | 0.2 | 29.4 | 16.1 | 54.3 |
| | | 48 | 5.2 | 0.3 | 38.5 | 20.4 | 40.9 |
| | | 96 | 5.2 | 0.3 | 50.4 | 25.0 | 24.3 |
| | | 168 | 5.1 | 0.5 | 58.2 | 28.4 | 13.0 |
| 20 | 100 | 4 | 5.2 | 0.2 | 23.6 | 10.8 | 65.5 |
| | | 24 | 5.1 | 0.3 | 48.9 | 15.8 | 35.0 |
| | | 48 | 5.0 | 0.3 | 59.3 | 18.7 | 21.7 |
| | | 96 | 5.0 | 0.4 | 68.1 | 20.2 | 11.3 |
| | | 168 | 4.8 | 0.4 | 72.4 | 20.0 | 7.3 |

From the table it is seen that only minimal amounts of glucose (DP$_1$) are produced by the β-amylase of the invention, and that the use of said β-amylase in combination with debranching enzymes such as pullulanase and isoamylase leads to syrups of high maltose content (DP$_2$).

We claim:

1. A beta amylase enzyme obtainable by cultivation in a suitable nutrient medium of Bacillus strain NCIB 11608, the enzyme being characterized by an inability to hydrolize maltotriose, by a pH optimum in the range of 4–5, and by an activity optimum at pH 4.5 of about 70° C.

2. A maltogenic amylase enzyme product in solid form which comprises the beta amylase obtainable by cultivation in a suitable nutrient medium of Bacillus straing NCIB 11608, the enzyme being characterized by an inability to hydrolyze maltotriose, by a pH optimum in the range of 4–5, and by an activity optimum at pH 4.5 of about 70° C.

3. A process for the preparation of a beta amylase enzyme wherein Bacillus strain NCIB 11608 or a variant thereof productive of this enzyme is cultivated in a suitable nutrient medium containing carbon and nitrogen sources and inorganic slats followed by recovery of the beta amylase enzyme from the culture broth.

4. An enzyme composition comprising a beta amylase obtainable by cultivation in a suitable nutrient medium of Bacillus strain NCIB 11608, the enzyme being characterized by an inability to hydrolyze maltotriose, by a pH optimum in the range of 4–5, and by an activity optimum at pH 4.5 of about 70° C. in combination with one or more debranching enzyme(s).

5. An enzyme composition according to claim 4 wherein the debranching enzyme is isoamylase or pulluanase.

6. A biologically pure culture of the Bacillus species of strain NCIB 11608.

* * * * *